United States Patent
Rapoport

(10) Patent No.: US 9,068,158 B2
(45) Date of Patent: Jun. 30, 2015

(54) MRD-BASED REACTORS

(75) Inventor: Uri Rapoport, Moshav Ben Shemen (IL)

(73) Assignee: ASPECT AI LTD., Moshav Ben Shemen (IL)

( * ) Notice: Subject to any disclaimer, the term of this patent is extended or adjusted under 35 U.S.C. 154(b) by 1370 days.

(21) Appl. No.: 12/279,736

(22) PCT Filed: Feb. 13, 2007

(86) PCT No.: PCT/IL2007/000201
§ 371 (c)(1),
(2), (4) Date: Aug. 18, 2008

(87) PCT Pub. No.: WO2007/093992
PCT Pub. Date: Aug. 23, 2007

(65) Prior Publication Data
US 2009/0197294 A1    Aug. 6, 2009

Related U.S. Application Data

(60) Provisional application No. 60/772,870, filed on Feb. 14, 2006.

(51) Int. Cl.
*C12M 1/34*    (2006.01)
*C12M 1/36*    (2006.01)
*G01N 24/08*   (2006.01)

(52) U.S. Cl.
CPC .............. *C12M 41/36* (2013.01); *C12M 41/48* (2013.01); *G01N 24/088* (2013.01); *C12M 41/46* (2013.01); *G01N 24/08* (2013.01)

(58) Field of Classification Search
CPC ...... C12M 41/36; C12M 41/46; C12M 41/48; G01N 24/08; G01N 24/088; G01R 33/46; G01R 33/465

USPC .............. 435/3, 29, 287.1, 288.7, 286.1; 436/173; 324/309, 321
See application file for complete search history.

(56) References Cited

U.S. PATENT DOCUMENTS

| 5,313,162 A | 5/1994 | De Graaf et al. |
| 5,862,060 A | 1/1999 | Murray, Jr. |

(Continued)

FOREIGN PATENT DOCUMENTS

| EP | 1500944    | 1/2005 |
| EP | 1500944 A1 | 1/2005 |

OTHER PUBLICATIONS

Meehan et al. "Cultivator for NMR Studies of Suspended Cell Cultures." Biotechnology and Bioengineering, vol. 40 (1992), pp. 1359-1366.*

(Continued)

*Primary Examiner* — William H Beisner
(74) *Attorney, Agent, or Firm* — Paul D. Bianco; Martin Fleit; Fleit Gibbons Gutman Bongini & Bianco PL

(57) ABSTRACT

The present invention depicts an MRD-based reactor. The MRD-based reactor comprises of a means for containing a flowing media and reacting the same (reactor). The reactor is characterized by a continuous wall portion, and is in connection with at least one MRD, adapted for applying localized spectroscopy towards the media. MRD-based reactors, in which the MRD is at least partially inside the reactor or reaction media, and those in which the MRD accommodates the reactor, are also introduced. Lastly, the invention teaches an in situ method for controlling and analyzing of a reaction. The method comprises of providing an MRD-based reactor; applying a magnetic field within the reactor, especially for performing a plurality of localized spectroscopic measurements and either real time or offline analyzing and/or controlling of reactions in the flowing media.

10 Claims, 12 Drawing Sheets

(56) References Cited

U.S. PATENT DOCUMENTS

| | | | |
|---|---|---|---|
| 6,103,934 | A | 8/2000 | Hallinan et al. |
| 6,228,650 | B1 | 5/2001 | Moore et al. |
| 6,395,538 | B1 * | 5/2002 | Naughton et al. .......... 435/288.7 |
| 6,979,308 | B1 | 12/2005 | MacDonald et al. |
| 2003/0210052 | A1 | 11/2003 | Okada et al. |
| 2004/0090231 | A1 | 5/2004 | Augustine et al. |
| 2009/0197294 | A1 | 8/2009 | Rapoport |

OTHER PUBLICATIONS

International Preliminary Report on Patentability published Mar. 10, 2009 for PCT/IL2007/000201 filed Feb. 13, 2007.
Written Opinion of the International Searching Authority published Mar. 6, 2009 for PCT/IL2007/000201 filed Feb. 13, 2007.
International Search Report published Apr. 16, 2009 for PCT/IL2007/000201 filed Feb. 13, 2007.
Castro et al., "Performance trade-offs in in Situ Chemostat NMR." Biotechnol. Prog., 15 (1999), pp. 185-195.
International Search Report and Written Opinion of the International Searching Authority mailed Feb. 7, 2013 for PCT/IL2012/000341.
International Preliminary Report on Patentability completed Dec. 17, 2013 for PCT/IL2012/000341.
European Communication dated Apr. 29, 2014 for Application No. 1783329.1-1560 (parallel EP application).
Ruizhen Chen and James E. Bailey; Observations of Aerobic, Growing *Eschenchia coli* Metabolism Using an On-Line Nuclear Magnetic Resonance Spectroscopy System; Biotechnology and Bioengineering; 1993; pp. 215-221; vol. 42.
A.J. Meehan, C.J. Eskey, A.P. Koretsky and M.M. Domach; Cultivator for NMR Studies of Suspended Cell Cultures; Biotechnology and Bioengineering; 1992; pp. 1359-1368; vol. 40.
Thomas-Helmut Scheper and Frank Lammers; Fermentation monitoring and process control; Current Opinion in Biotechnology; 1994; pp. 187-191; vol. 5.
Sascha Beutel and Steffen Henkel: In situ sensor techniques in modern bioprocess monitoring; Appl. Microbial Biotechnol.; 2011; pp. 1493-1505; vol. 91.
Paul D. Majors, Jeffrey S. McLean and Johannes C.M. Scholten; NMR bioreactor development for live in-situ microbial functional analysis; Journal of Magnetic Resonance; 2008; pp. 159-166; vol. 192.
Catherine Sarazin, Francoise Ergan, Jean-Paul Seguin, Gerard Goethans, Marie Dominique Legoy and Jean-Noel Barbotin; NMR on-Line Monitoring of Esterification Catalyzed by Cutinase; Biotechnology and Bioengineering; 1995; pp. 636-644; vol. 51.
L. Brecker, H. Weber, H. Griengl and D.W. Ribbons; in situ proton-Nmr analyses of *Escherichia coli* HB101 fermentation in 1H20 and in D20; Microbiology; Dec. 1999, pp. 3389-87.
Supplementary Search Report for EP Application No. 07706143 dated Mar. 8, 2013.

* cited by examiner

MRD-BASED REACTORS

FIELD OF THE INVENTION

The present invention generally relates to an on-line and in situ MRD-based (Magnetic Resonance Detector) reactor for real-time analysis and/or control of a reaction or fermentation. More specifically, the present invention is adapted for applying localized spectroscopy means in the reaction media and/or outside said media.

BACKGROUND OF THE INVENTION

In the early state of the art, fermentation processes were carried out on surfaces of solid media. However, surface fermentations are costly and difficult to operate. Thus, liquid or submerged fermentation evolved. The vessels used in submerged fermentation are called fermentors or bioreactors (the latter is preferably used when the vessel is designed for the culturing of tissue cells).

A fermentor is a vessel designed for the cultivation of microorganisms. The environment in the vessel is closely controlled to enable the proper expression of biochemical reactions for the production of the desired by-product.

In a CSTR (Continuous Stirred-Tank Reactor), one or more fluid reagents are introduced into a tank reactor equipped with an impeller while the reactor effluent is removed. The impeller stirs the reagents to ensure proper mixing.

In a PFR (Plug Flow Reactor), one or more fluid reagents are pumped through a pipe or tube. The chemical reaction proceeds as the reagents travel through the PFR.

U.S. Pat. No. 6,103,934 to Hallinan et al. discloses a process control method for producing acetic acid by catalyzed carbonylation of methanol in which various reactor component concentrations, e.g., active catalyst, methyl iodide, water and methyl acetate are measured using an infrared analyzer. The concentrations are adjusted in response to the measurements taken to optimize the acetic acid reaction.

U.S. Pat. No. 6,228,650 to Moore et al. discloses controlling concentration of alkylation catalyst components Hydrofloric acid, acid soluble oil (ASO) and water, by measuring a continuously flowing catalyst slipstream in an IR analyzer and using the results to vary the temperature of stripping fluid in order to control ASO levels within a preferred range.

U.S. Pat. No. 5,862,060 to Murray, Jr. discloses controlling chemical processes using compositional data, as the basis for control using NIR (Near InfraRed) spectroscopy which allows for on-line measurements in real time. A calibration set of NIR spectra binding the acceptable process space for a particular controlled property is assembled and a multi-variant statistical method is applied to the calibration step to identify a small number (2-4) of the characteristics of the set governing the controlled property. Thus a complex process can be controlled in such a way as to provide a substantially invariant product composition.

Fermentor design has not changed radically over the years; however, user requirements are becoming increasingly sophisticated and complex, thus accentuating the need for improved culture vessels and systems.

Electromagnetic based instruments for measuring properties of matter or identifying its composition are well known. Magnetic resonance spectroscopy is one of the principal measuring techniques used to obtain physical, chemical and structural information about a molecule.

The present invention is intended to provide an on-line and in situ MRD-based reactor for analysis and/or control of a reaction provided in a reactor which overcomes several shortcomings of fermentors and fermentation methods of the current technology. Particularly, this invention provides an MRD-based reactor for real-time analysis and/or control of a reaction or fermentation.

More specifically, the present invention is adapted for applying localized spectroscopy means in the reaction media and/or outside said media.

None of these prior art references disclose a reactor that utilizes MRD spectroscopy for analyzing and controlling on-line and in situ a reaction provided in a reactor in real-time. Also, none of the literature cited teaches the adaptation of such reactor for applying localized spectroscopy means in the reaction media and/or outside the media.

SUMMARY OF THE INVENTION

It is therefore one object of the present invention to disclose an MRD-based reactor which comprises of a means for containing a flowing media and reacting the same (i.e., reactor). The MRD-based reactor is characterized by a continuous wall portion, wherein the reactor is in connection with at least one MRD adapted for applying localized spectroscopy towards the media. It is in the scope of the invention wherein the localized spectroscopy is applied inside and/or outside the reaction media.

It is in the scope of the invention wherein the MRD (1) is at least partially accommodated within the reactor (119); or wherein the reactor is at least partially accommodated within the MRD.

It is also in the scope of the invention wherein the MRD (1) is at least temporarily immersed within the flowing media, and characterized by at least one tubular sampling cavity (6) within which the flowing media (7) is contained and a homogenous magnetic field is applied.

It is also in the scope of the invention wherein the immersible MRD (1) is removably mounted within the container in either an immobilized manner or a maneuverable manner.

It is also in the scope of the invention wherein an MRD-based reactor (103) is disclosed. The MRD (1) is integrally incorporated within the container (119) or attached to at least one of its modules, especially the impeller shaft, ventilation tube or baffles or any other instrument that regulates flow.

It is also in the scope of the invention to present a jacketed MRD-based reactor as defined above. The jacketed MRD-based reactor comprises of at least one reactor accommodated within at least one enveloping jacket, wherein at least one jacket is the MRD.

It is also in the scope of the invention wherein the MRD is provided as the reactor's wall.

It is also in the scope of the invention wherein the MRD is enveloped by at least a first and a second layer. The first layer is isolating the MRD from the reaction media, and the second layer comprises the MRD's magnets.

It is also in the scope of the invention wherein the aforesaid MRD's first layer is made of a metal such as stainless steel, metal alloy or any combination thereof.

It is also in the scope of the invention wherein the MRD is adapted to target at least one specific volume of interest within the reaction media and to analyze the same.

It is also in the scope of the invention wherein the MRD-based reactor (104) comprises of a plurality of n apertures (104A-104N), preferably where n is between 1 and 4, provided in the magnetic walls, enabling a clear view and access to the reactor (103) from its surroundings.

It is also in the scope of the invention wherein the MRD-based reactor as defined in any of the above further comprises of modules selected from a group consisting of at least one sensor; a motor; and an impeller adapted to ensure adequate mixing of the flowing media, such that homogenous magnetic field is applied within the MRD.

It is also in the scope of the invention wherein the MRD-based reactor as defined in any of the above comprises of an MRD which is characterized by a multilayered structure comprising a closed magnetic circuit constructed from strong permanent magnets (1a-1c); an optional shimming mechanism (2); a global gradient coil (3); an array of local gradient coils (4a-4c); and a contained cavity (12) into which the reactor is introduced.

It is also in the scope of the invention wherein the MRD is an open tube with a shape that is selected from a group consisting of polygonal, trapezoid, cuboid, or especially cylindrical, or any combination thereof.

It is also in the scope of the invention wherein the reactor is a member with a shape that is selected from a group consisting of polygonal, trapezoid, cuboid, or especially cylindrical, or any combination thereof.

It is also in the scope of the invention wherein the reactor is an universal laboratory high-speed spinning equipment.

Another object of the invention is to disclose an in situ method for controlling and analyzing of flowing media. The method comprises of steps selected from providing an MRD-based reactor comprising means for containing a flowing media and reacting the same (reactor), characterized by a continuous wall portion, wherein the reactor is in connection with at least one MRD adapted for applying localized spectroscopy towards the media; applying a magnetic field within the reactor; especially for performing a plurality of localized spectroscopic measurements; and, either real time or offline analyzing and/or controlling of reactions in the flowing media.

It is also in the scope of the invention wherein the D-based reactor is optionally adapted for controlling at least one process variable or reaction point at a specified process point or for controlling several process variables concurrently or for controlling the variable at several process points and/or any combination thereof.

BRIEF DESCRIPTION OF THE FIGURES

In order to understand the invention and to see how it may be implemented in practice, several embodiments will now be described, by way of non-limiting examples only, with reference to the accompanying drawings, in which FIG. 1 schematically represents a cross section of fermentor (10) as known in prior art.

DETAILED DESCRIPTION OF PREFERRED EMBODIMENTS

Figure 1:
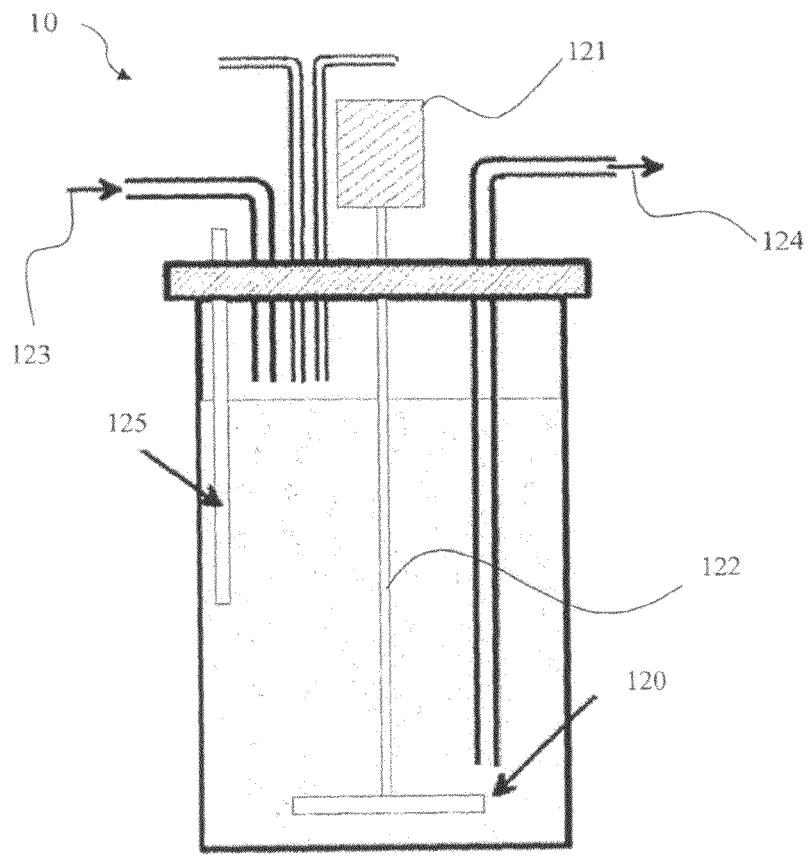

The following description is provided, alongside all chapters of the present invention, so as to enable any person skilled in the art to make use of the invention and sets forth the best modes contemplated by the inventor of carrying out this invention. Various modifications, however, will remain apparent to those skilled in the art, since the generic principles of the present invention have been defined specifically to provide an on-line and in situ MRD-based reactor for real-time analysis and/or control of a reaction or fermentation, adapted for applying localized spectroscopy means in the reaction media and/or outside the media.

This application focuses on spectroscopy as an analytical technique capable of giving truly real-time compositional data. Spectroscopic measurements are performed continuously in situ and on-line and unique and useful compositional information of any particular product is usually available from several regions of the electromagnetic spectrum.

The term 'magnetic resonance detector' (MRD) applies hereinafter to any Magnetic Resonance Imaging (MRI) device, any Nuclear Magnetic Resonance (NMR) spectroscope, any Electron Spin Resonance (ESR) spectroscope, any Nuclear Quadrupole Resonance (NQR) or a combination thereof.

The term 'flowing media' applies hereinafter to any flowing matter, before, after or in the process of a reaction. The media is selected in a non-limiting manner from a group consisting of gas, liquid, flowing solids such as particles, especially nanoparticles and micronic particles, sols, gels, sol-gels, colloids, emulsions, suspensions, dispersions, liposomes, aggregates, crystals, cells including red cells and stem cells, seeds, or a combination thereof.

The term 'gradient coil' applies hereinafter to a coil used to create a magnetic gradient in at least one direction and that can be used for localized measurement of the sample cavity.

The term 'Reactor' applies hereinafter to chemical, biological and/or physical reactors or fermentors, namely to vessels that are designed for chemical, biological and/or physical reaction to occur inside of them. The reactor normally yet not exclusively characterized as a tank reactor—a tank that is usually enclosed to keep contaminants out of the reaction vessel, or envelope, tubular reactor—a pipe or tube or a combination thereof. Both types can be used according to the present invention as continuous reactors or batch reactors. The reactor may run at steady-state, but can also be operated in a transient state. The reactor may accommodate one or more solids (reagents, catalyst, or inert materials), but the reagents and products are typically liquids and gases. Preferably, yet not exclusively, the media is liquid.

According to one embodiment of the present invention, the reactor as defined above is a CSTR. In the CSTR, one or more fluid reagents are introduced into a tank reactor equipped with an impeller while the reactor effluent is removed. The impeller stirs the reagents to ensure proper mixing. Simply dividing the volume of the tank by the average volumetric flow rate through the tank gives the residence time, or the average amount of time a discrete quantity of reagent spends inside the tank. Using chemical kinetics and or biological-driven kinetics (e.g., enzymes, whole-cell enzymes and producing microorganism) the reaction's expected percent completion can be calculated. It is in the scope of the present invention wherein at steady-state, the flow rate in equals the mass flow rate out, According to another embodiment of the present invention, the reactor as defined above is a PFR. In a PFR, one or more fluid reagents are pumped through a pipe or tube. The chemical reaction and/or biological bio-reaction proceeds as the reagents travel through the PFR. In this type of reactor, the reaction rate is a gradient; at the inlet to the PFR the rate is very high, but as the concentrations of the reagents decrease and the concentration of the product(s) increases the reaction rate slows.

According to another embodiment of the present invention, the reactor is a column, e.g., distillation or extraction column.

The term 'reaction' refers also to biological or biotechnological-oriented reactions and processes, e.g., bioreaction and fermentations; and to various chemical reactions or processes, e.g., distillations, evaporations, extractions, halogenations, etherifications, esterifications, saponifications, transesterifications, precipitations, oil refining, etching, and various analytical methods, processes and reactions. The term relates also to physical processes, such as milling, extruding, molding, pressing, gnawing, nibbling, heat exchanging, photocatalytic reactions and processes, nuclear reactions etc.

The term 'liquid' applies hereinafter to aqueous solutions, non-aqueous solutions, water-miscible solutions, water-immiscible solutions, oil solutions, non-critical solutions, critical solution, emulsions, suspensions and/or dispersions of one liquid within another, aggregated liquids, fluids or in any combination thereof.

The term 'plurality' applies hereinafter to any integer greater than or equal to one. The term 'about' refers hereinafter to a tolerance of ±20% of the defined measurement.

Reference is made now to FIG. 1, schematically illustrating a cross-section of a commercially available batch wise, aerobic or anaerobic, continuous or semi-continuous, one phase or multiple phased reactor (e.g., a fermenter) (10). The fermentor comprises various modules, such as a rotating impeller (120), actuated by an external motor (121). The impeller and the motor are physically communicated by an elongated, usually perpendicular axle (122). The impeller is adapted to homogenise the reaction media (e.g., the fermented broth). Raw materials, e.g., nutrients; catalysts, e.g., enzymes, inoculum or microbial culture, buffers, by products, oxygen etc., are fed into the reaction media via at least one inlet (123), whereas by products, products, samples, purge etc. are evacuated from the reaction via at least one outlet (124). Sensors, aerators and other auxiliaries are soaked in said reaction media or adjacent to the same (125). External facilities are also provided useful, e.g., heat exchange jacket, shakers etc (not shown).

Figure 2:
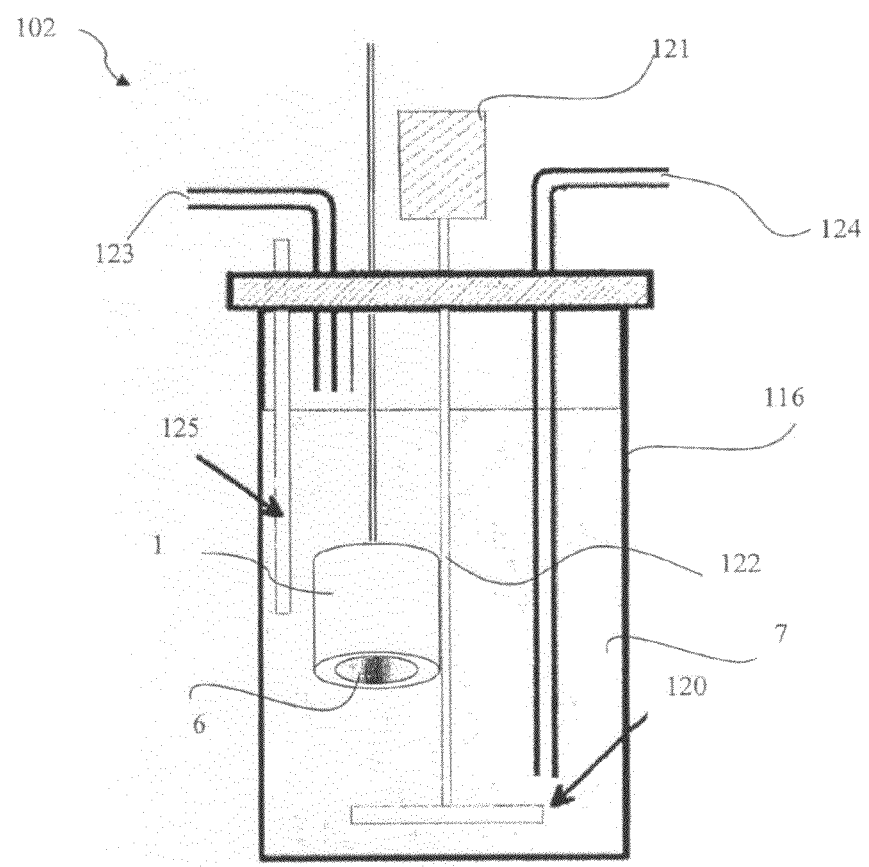
FIG. 2 schematically represents a cross section of the reactor (102) according to one embodiment of the current invention.

Reference is made now to FIG. 2, schematically presenting a cross section of a MRD-based reactor (102) according to another embodiment of the current invention. MRD (1) is immersed in the reaction media (7) in the reactor (116). Here for example and in a non-limiting manner, the magnetic resonance device is a cylindrical open tube with a sampling cavity (6). MRD (1) is hence adapted to be reversibly, temporarily or fixedly dipped inside the media, providing online, continuous in situ analysis and feedbacked control for the reaction. The MRD-based reactor additionally comprises an inlet (123) and outlet (124) for the reaction media, an impeller (120) and its axle (122) and motor (121) to power the impeller and a sensor (125) soaked in the reaction media.

Figure 3:
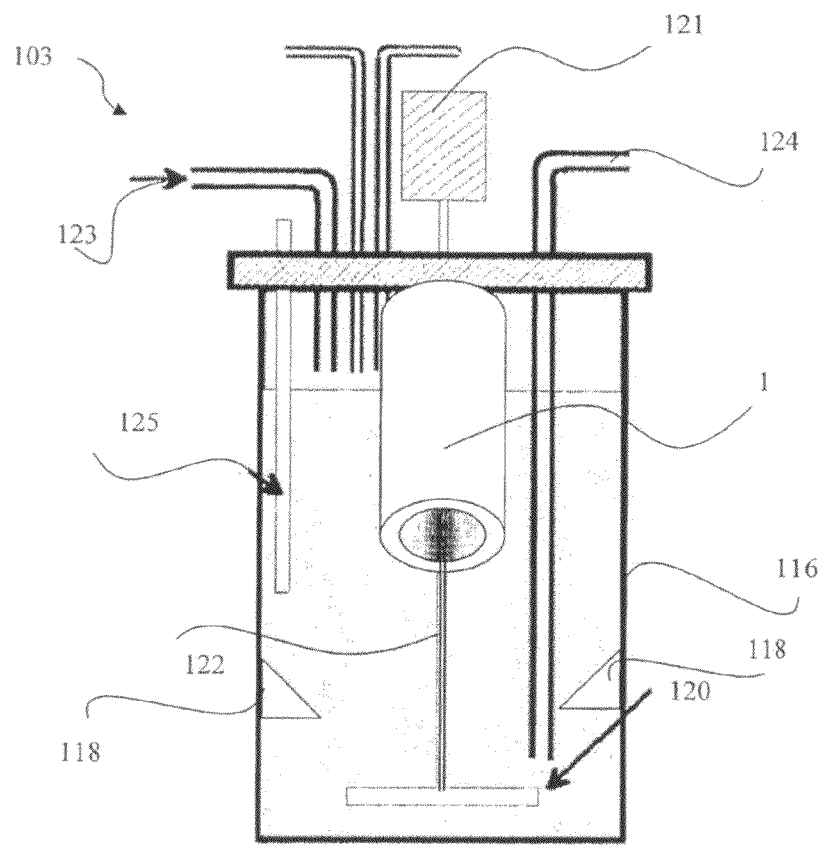
FIG. 3 schematically represents a cross section of the reactor (103) according to another embodiment of the current invention.

Reference is made now to FIG. 3, schematically presenting a cross section of a MRD-based reactor (103) according to another embodiment of the current invention. Said MRD (1) is immersed and localized on the axle (122) of the said impeller (120) inside the reactor media (7) in the reactor (116). There is an inlet (123) and an outlet (124) for the reaction media and a sensor (125) is soaked in the reaction media. Here, for example and in a non-limiting manner, the MRD is a cylindrical open tube integrated to one of the reactor's modules, e.g., impeller's axle. The MRD can alternatively or additionally be affixed to other modules or locations, e.g., the reactor's baffles (18) etc.

In the example described above, the MRD is located at least partially inside the reactor and/or inside the reaction media. It is further in the scope of the invention wherein the MRD is located in the external side of the reactor or outside the reaction media.

Figure 4A:
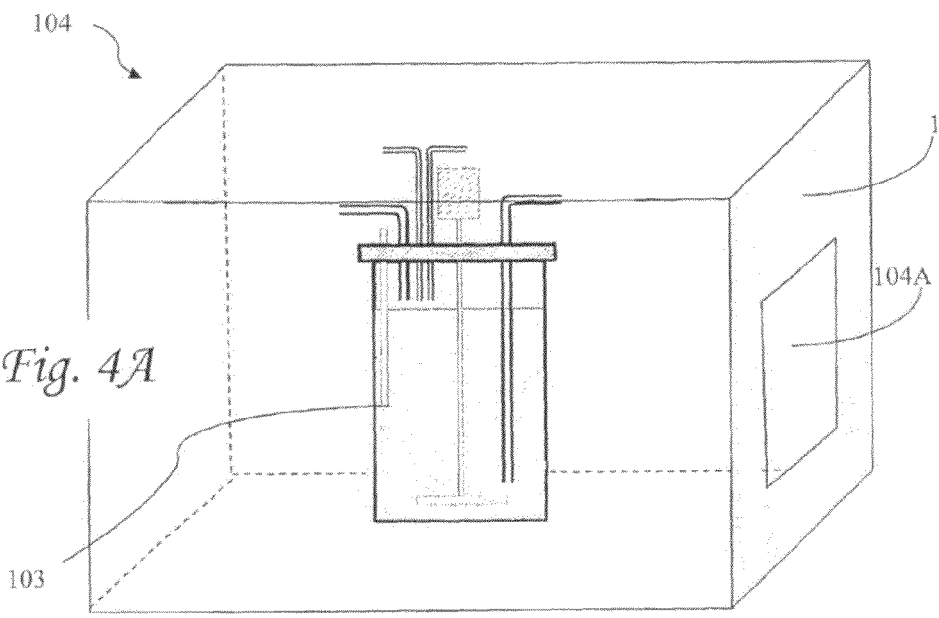
FIG. 4A schematically represents a cross section of the reactor (104) according to another embodiment of the current invention.

Reference is made thus to FIG. 4A, schematically presenting a 3D illustration of an MRD-based reactor (104) according to another embodiment of the current invention. An MRD is localized outside said reactor (103). MRD (1) is e.g., a cuboid jacket (1) enveloping the reactor (103), that is accommodated in-between the MRD's magnetic walls. The MRD also has at least one aperture (104A), preferably a plurality of windows, e.g., 1 to 4 windows, provided in said walls, enabling a clear view and access to the reactor and from the reactor to its surroundings.

Figure 4B:
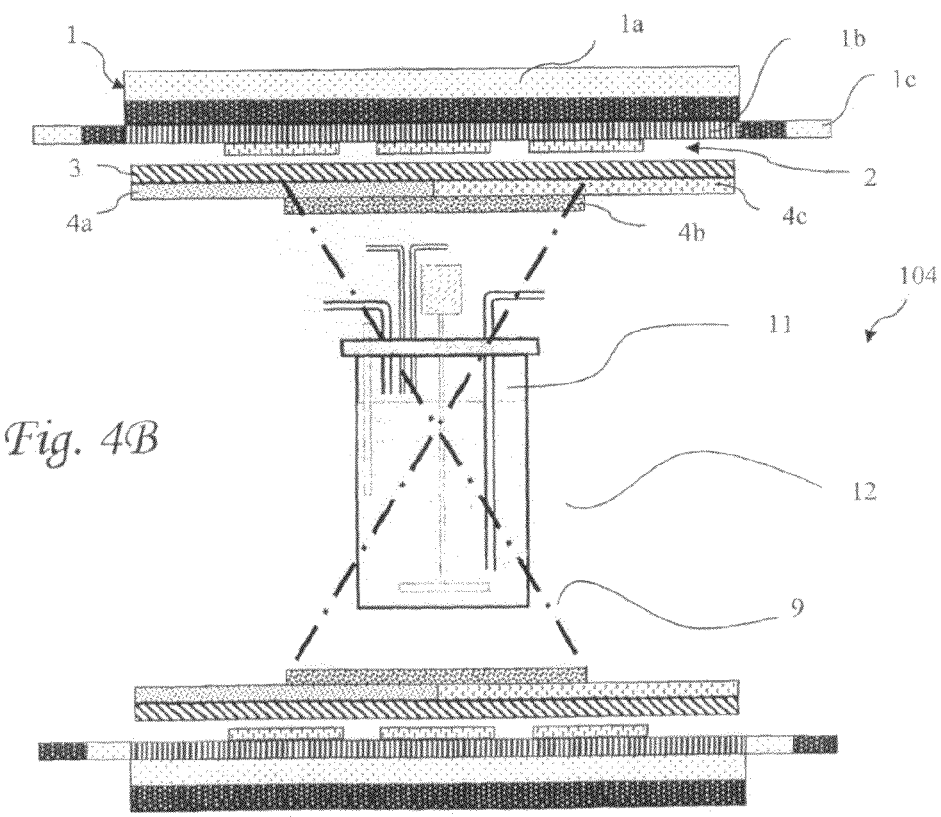
FIG. 4B schematically represents a cross section of the reactor (11) through the magnetic resonance device showing the magnetic field in the sample cavity produced by the closed magnetic circuit magnets, according to another embodiment of the current invention.

Reference is made now to FIG. 4B, schematically representing a cross section of an MRD based reactor (104, the reactor (11) being inside the magnetic resonance detector (1). The MRD is localized outside said reactor media. FIG. 4B shows the magnetic field produced by the closed magnetic circuit magnets. The magnetic field gradient, (9), produced by local gradient coils (4a and 4c) and local central gradient coil (4b), passing through the reactor, (11), which has been introduced into the sample cavity (12), according to another embodiment of the current invention. A closed magnetic circuit, (1), comprises a large permanent magnet (1a), a pole piece (1b) and an array of side wall magnets (1c). A shimming mechanism (2) is used to maintain uniform magnetic field within the cavity. A global gradient coil (3) extends along the length of the sample cavity. An array of local gradient coils, (4), are positioned at intervals along the length of the cavity and overlap such that any volume section within the sample cavity is within the field of at least one of the local gradient coils.

In the following few examples, including FIGS. 5 and 6, the MRD of the present invention is being adapted to serve as the reactor's envelope. The reaction is at least partially accommodated within said MRD, such that the MRD is the reactor. Alternatively, the MRD is in an integral or at least temporary connection with an adjacent reactor.

Figure 5:
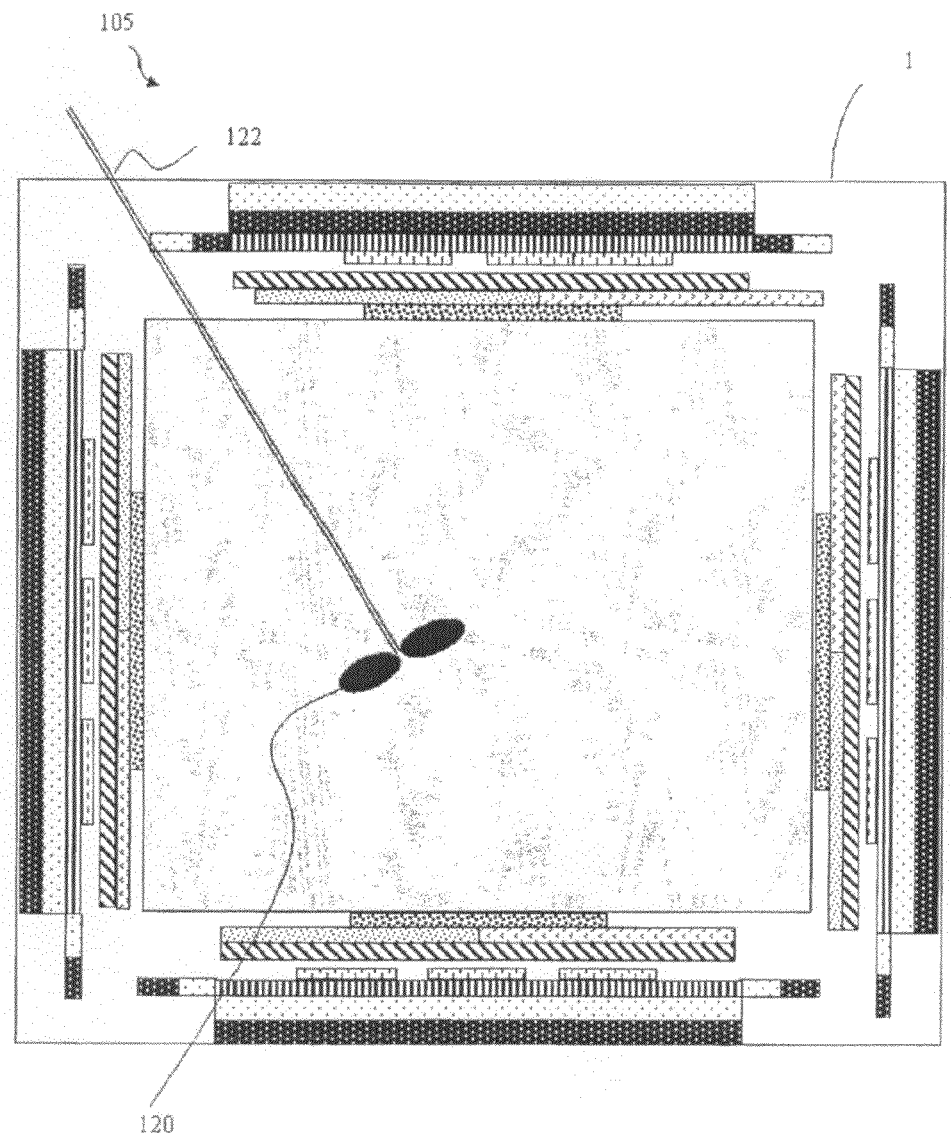
FIG. 5 schematically represents a cross section of the reactor (105) throughout the sample cavity according to another embodiment of the current invention.

Reference is made now to FIG. 5, schematically presenting a segmental cross-section of a rectangular, polygonal or cuboid MRD-incorporated reactor (105) throughout the sample cavity according to another embodiment of the current invention. The reaction media (126) is accommodated in said MRD (1). The reactor also contains an impeller (120) and axle (122). Here for example and in a non-limiting manner, the MRD is cuboid and the reactor media is cuboid too.

Figure 6:
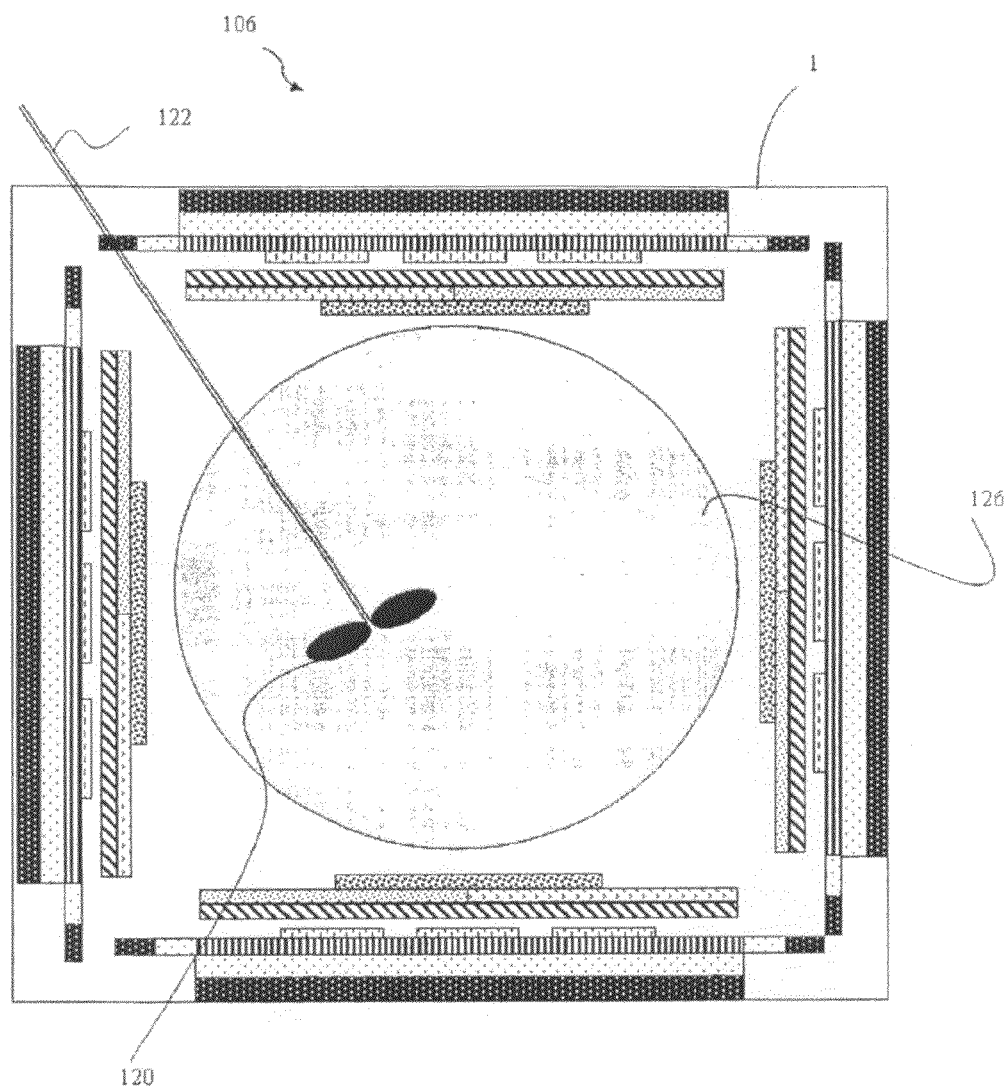
FIG. 6 schematically represents a cross section of the reactor (106) throughout the sample cavity according to another embodiment of the current invention.

Reference is now made to FIG. 6, schematically presenting a segmental cross-section of a MRD-based reactor (106) throughout the sample cavity according to another embodiment of the current invention. The reaction media (126) is accommodated in said MRD. The reactor also contains an impeller (120) and axle (122). Here for example and in a non-limiting manner, the MRD is cuboid and the reactor media is cylindrical.

Figure 7:
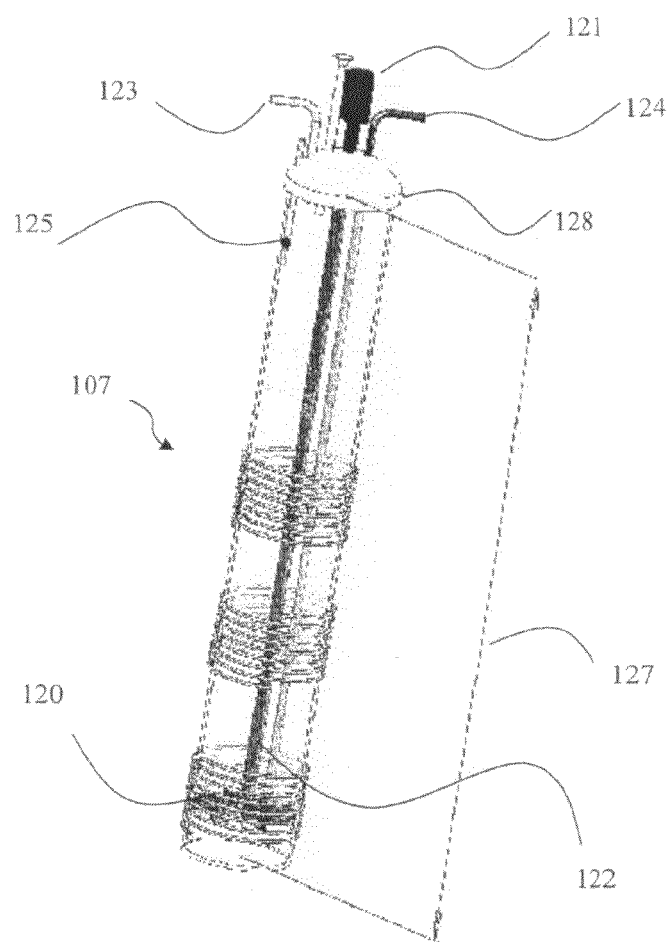
FIG. 7 schematically represents a perspective view of one optional column-like reactor (107)
Figure 8:
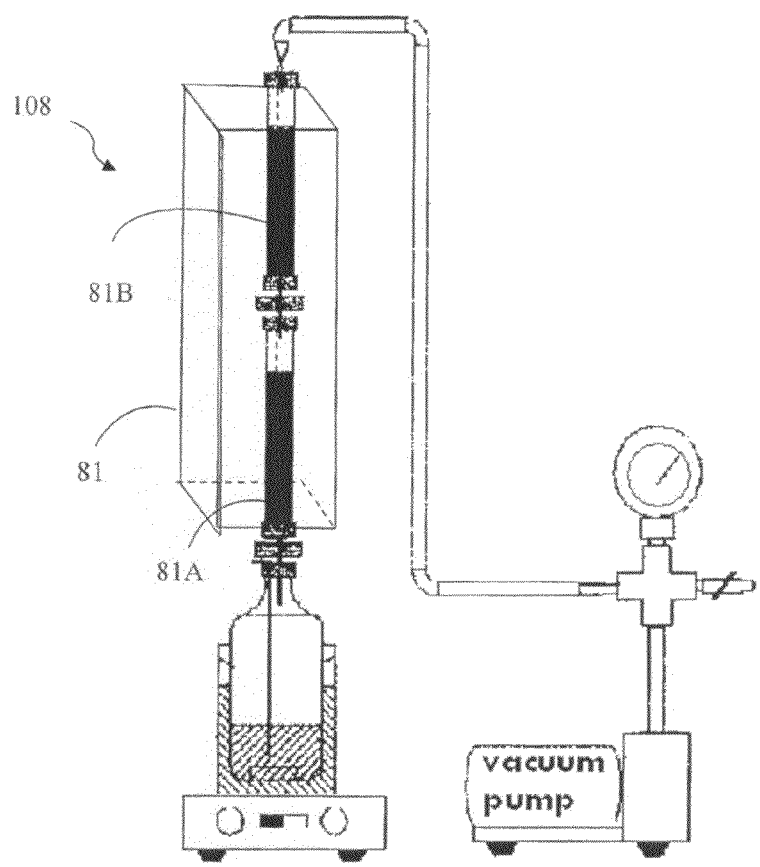
FIG. 8 schematically represents a perspective view of reactor (107) in an MRD (81)
Figure 9:
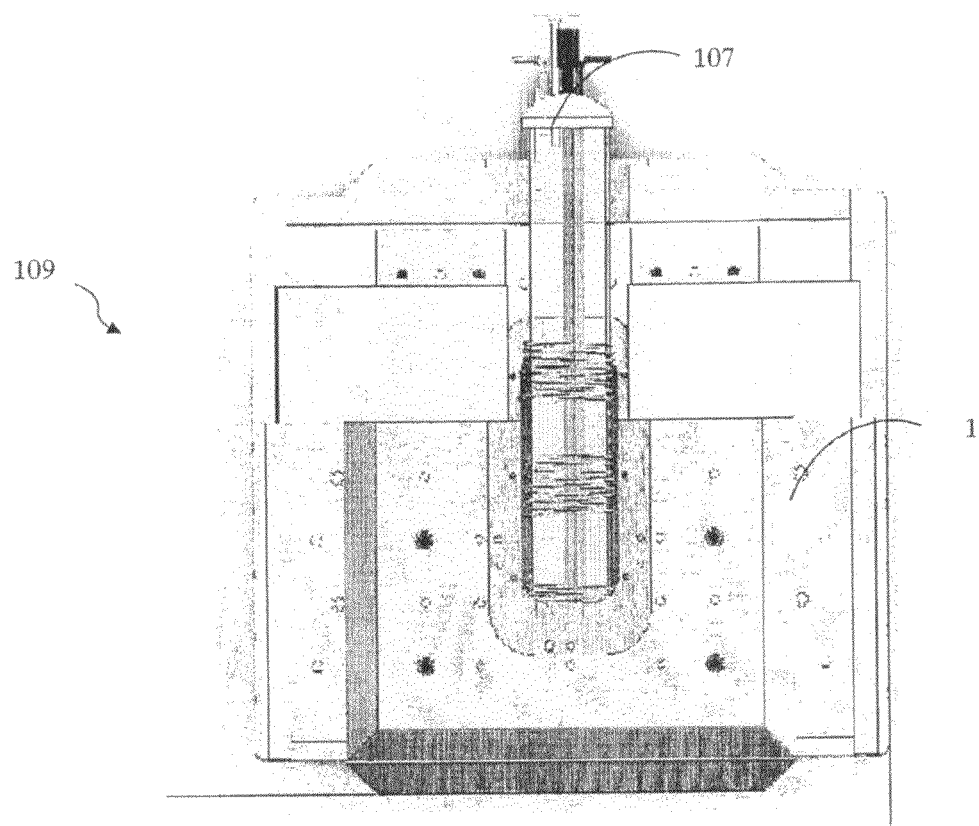
FIG. 9 schematically represents a perspective view of an MRD-reactor system according to another embodiment of the present invention.

It is further in the scope of the present invention wherein the reactor is characterized by an elongated tube-like shape. Referring now to FIG. 7, a tubular reactor (107) is illustrated for example, in one embodiment the tubular reactor may have a main longitudinal axis (127), of about 16 inches and an external diameter (128) of about 3 inches. A similar reactor (108) which is useful, for example, for liquid-liquid extraction of a set of two-plates distillation column (See 81A and 81B) is depicted in FIG. 8. The two distillation plates are at least partially enveloped by an elongated MRD (81). Alternatively or additionally, an MRD-based analysis and/or control system (109) is presented in FIG. 9, wherein said elongated reactor (107) is partially accommodated within MRD (1), e.g., 20 inches by 20 inches. Here, the agitated reaction media in the reactor is in situ and continuously monitored by the MRD device, while free access to the reactor is provided.

Figure 10:
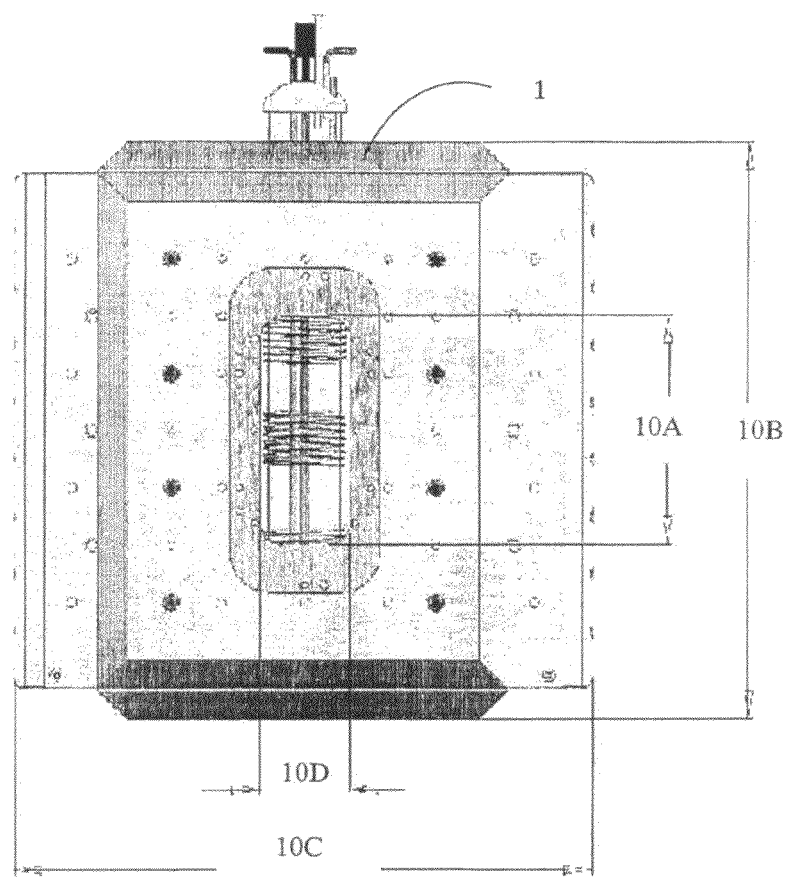
FIG. 10 schematically represents a side view of an MRD-reactor system according to this embodiment of the present invention.
Figure 11:
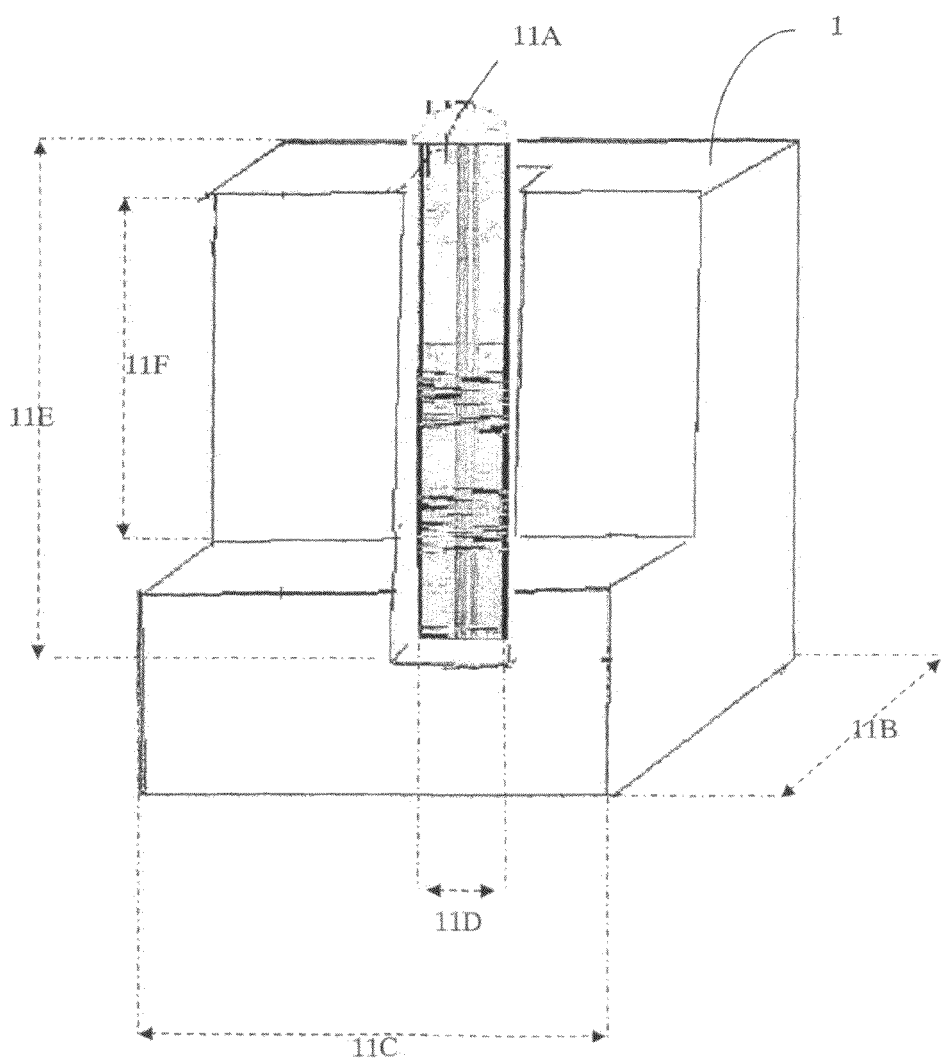
FIG. 11 schematically represents a partial cross-section (lateral-) view of an MRD-reactor system according to this embodiment of the present invention; and, FIG. 12 schematically represents a lateral view of a continuous MRD-extruding system according to another embodiment of the present invention.

Reference is now made to FIG. 10, illustrating a similar system wherein an aperture (one or more) is provided in MRD (1) wherein the proportion of the MRD and the reactor, namely e.g., the MRD's height (10B), and width (10C) is proportional to the said aperture's height (10A) and width, e.g., in accordance with the aforesaid example, 10A-10D is 8 inches, 20 inches, 20 inches and 3.5 inches, respectively. Another view of the same is provided in an illustrative manner in FIG. 11, wherein 11A-11F is 3.5 inches, 18 inches, 20 inches, 3.5 inches, 20 inches and 8 inches, respectively and accordance with the above mentioned example.

Figure 12:
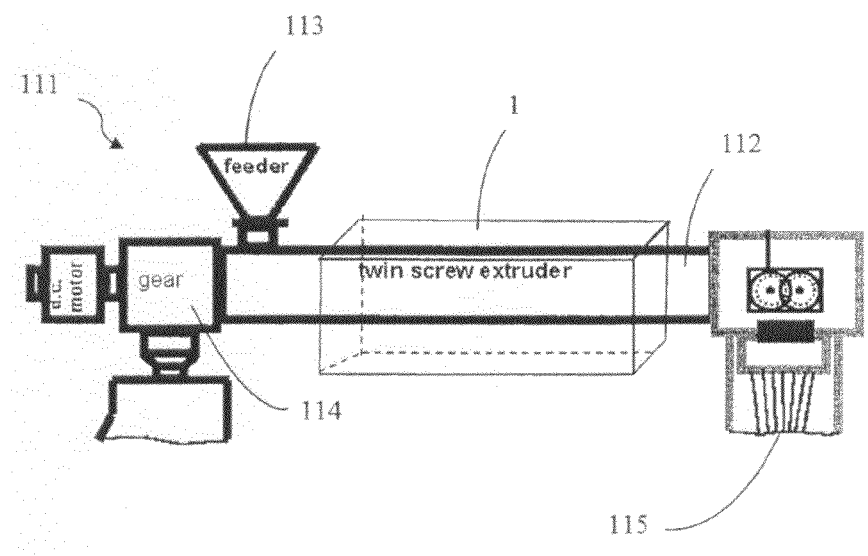

Lastly, reference is made to FIG. 12, illustrating a lateral view of a continuous MRD-based reactor (111), namely, yet in a non-limiting manner, the reactor is a universal laboratory high speed spinning equipment, combined with a single twin screw extruder (112) in communication with a monomer raw materials feeder (113). The screw is rotating by motor and gear (114), and with a polymeric fiber outlet (115).

The invention claimed is:

1. A Magnetic Resonance Imaging Detector (MRD)-based reactor comprising:
    a reactor vessel containing a reactant media;
    an impeller for mixing said reactant media in said reactor vessel such that said reactant media is substantially uniformly mixed, and
    a magnetic resonance detector (MRD) at least partially mounted in said reactor vessel, comprising a sampling cavity and generating a substantially homogeneous magnetic field within said sampling cavity;
    wherein said MRD applies localized spectroscopy on a portion of said uniformly mixed reactant media contained within said sampling cavity for analyzing and controlling fermentation of said portion of said uniformly mixed reactant media and obtaining real-time compositional data of said portion of said uniformly mixed reactant media.

2. The MRD-based reactor according to claim 1, wherein said MRD comprises:
    at least two permanent magnets for generating said substantially homogeneous magnetic field in said sampling cavity located between said at least two permanent magnets;
    a shimming mechanism for maintaining homogeneity of said magnetic field at edges of said at least two permanent magnets, and
    an array of local gradient coils for generating a variable magnetic field within said sampling cavity.

3. The MRD-based reactor according to claim 1, wherein said reactor vessel comprises:
    an inlet port for supplying said reactant media to said reactor vessel, and
    an outlet port for evacuating reaction products from said reactor vessel.

4. The MRD-based reactor according to claim 1, wherein said MRD is at least partially immersed in said reactant media.

5. The MRD-based reactor according to claim 4 said MRD is enveloped by an isolation layer for isolating said MRD from said reactant media.

6. The MRD-based reactor according to claim 1 wherein said MRD has a geometrical shape said geometrical shape is selected from the group consisting of a polygon, a cylinder, a trapezoid, a cuboid and any combination thereof.

7. The MRD-based reactor according to claim 1 wherein said reaction vessel has a geometrical shape said geometrical shape is selected from the group consisting of a polygon, a cylinder, a trapezoid, a cuboid and any combination thereof.

8. The MRD-based reactor according to claim 1 wherein said uniformly mixed reactant media comprises flowing media, said flowing media is selected from the group consisting of a fluid, a gaseous medium, a liquid, a flowing solid, a colloid, said colloid is selected from the group consisting of nano-particles and micronic particles, sols, gels, sol-gels, emulsions, suspensions, dispersions, liposomes, aggregates, crystals, cells, said cells are selected from the group consisting of red cells and stem cells, seeds and any combination thereof.

9. A method for analyzing reactant media comprising:
    providing a Magnetic Resonance Detector (MRD)-based reactor, said MRD-based reactor comprising a reactor vessel and a magnetic resonance detector;
    supplying said reactant media to said reactor vessel via an input port;
    generating a substantially uniformly mixed reactant media by mixing said reactant media in said reactor vessel;
    generating by means of said MRD at least partially immersed within said reactant media a homogeneous magnetic field within a sampling cavity of said MRD for performing localized spectroscopy on a fermenting process of said uniformly mixed reactant media contained within said sampling cavity;
    analyzing results of spectroscopic measurements said analyzing results is selected from the group consisting of analyzing results in real-time, analyzing results on-line and analyzing results off-line;
    evacuating reaction products from said reactor vessel via an outlet port, and
    employing said analyzed results for controlling said fermenting process of said uniformly mixed reactant media in said reactor vessel.

10. The method for analyzing reactant media according to claim 9 said controlling at least one parameter of said fermentation process said controlling of at least one parameter is selected from the group consisting of controlling said at least one parameter of said fermentation process simultaneously and controlling said at least one parameter of said fermentation process asynchronously.

* * * * *